United States Patent [19]

Klemmensen et al.

[11] Patent Number: 5,986,130
[45] Date of Patent: Nov. 16, 1999

[54] PROCESS FOR THE PREPARATION OF CYCLOPROPANE CARBOXYLIC ACIDS AND INTERMEDIATES THEREFOR

[75] Inventors: Per Dausell Klemmensen; Hans Kolind-Andersen; Ib Winckelmann, all of Lemvig, Denmark

[73] Assignee: Cheminova Agro A/S, Harboor, Denmark

[21] Appl. No.: 09/000,034

[22] PCT Filed: Jul. 17, 1996

[86] PCT No.: PCT/DK96/00326

§ 371 Date: Jan. 20, 1998

§ 102(e) Date: Jan. 20, 1998

[87] PCT Pub. No.: WO97/03941

PCT Pub. Date: Feb. 6, 1997

[30] Foreign Application Priority Data

Jul. 21, 1995 [DK] Denmark ................... 0854/95

[51] Int. Cl.⁶ ...................................... C07C 61/04
[52] U.S. Cl. ........................ 562/506; 560/124; 549/302
[58] Field of Search ................. 560/124; 562/506; 549/302

[56] References Cited

U.S. PATENT DOCUMENTS

| 4,230,891 | 10/1980 | Verbrugge et al. | 568/591 |
|---|---|---|---|
| 4,281,182 | 7/1981 | Martel et al. | 562/506 |
| 4,333,950 | 6/1982 | Engel | 424/305 |

FOREIGN PATENT DOCUMENTS

| 2849/78 | 6/1978 | Denmark . |
|---|---|---|
| 5633/78 | 12/1978 | Denmark . |
| 2-0269514 | 6/1988 | European Pat. Off. . |
| 2000764 | 3/1977 | United Kingdom . |

OTHER PUBLICATIONS

Chem Abstracts 109:190585, Fujita et al., 1987.
M. Fujita, et al., *Tetrahedron Letters*, vol. 27, No. 19, 1986, pp. 2139–2141.
M. Fujita, et al., *Bull Chem. Soc.*, vol. 60, 1987, pp. 4385–4394.
A. K. Mandal, et al., *Tetrahedron*, 42, 5715, (1986).
D. Bakshi, et al., *Tetrahedron*, 45, 767–774, (1989).

*Primary Examiner*—Samuel Barts
*Attorney, Agent, or Firm*—Jacobson, Price, Holman & Stern, PLLC

[57] ABSTRACT

The compounds 3-(2,2-dichloro-3,3,3-trifluoro-1-hydroxypropyl)-2,2-dimethyl-(1R,cis)-cyclopropane carboxylic acid, cis-3-(2,2-dichloro-3,3,3-trifluoro-1-hydroxypropyl)-2,2-dimethyl-cyclopropane carboxylic acid and (1R,5S)-4-(1,1-dichloro-2,2,2-trifluoroethyl)-6,6-dimethyl-3-oxabicyclo[3.1.0]hexan-2-one occur as intermediates in a process for the preparation of insecticidally active cyclopropane carboxylate esters, said process starting from 6,6-dimethyl-4-hydroxy-3-oxabicyclo[3.1.0]hexan-2-one (Biocartol) which is reacted with the compound $CF_3$—$CClX_2$ (X=halogen) in the presence of zinc.

19 Claims, No Drawings

PROCESS FOR THE PREPARATION OF CYCLOPROPANE CARBOXYLIC ACIDS AND INTERMEDIATES THEREFOR

This application is a 371 of PCT/DK96/00326 filed Jul. 17, 1996.

The present invention relates to compounds usable as intermediates in the preparation of cyclopropane carboxylic esters, and the invention also relates to processes for preparing these compounds.

Cyclopropane carboxylate esters are insecticidally active compounds which are known as "pyrethroids", and since they combine exceptionally good insecticidal properties with very low toxicity to mammals they are of considerable interest. Therefore, much effort has been made in order to find economically favourable routes for preparing them and their most important intermediates.

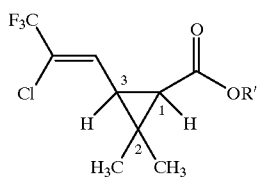

Ia: 1R, cis, Z
Ib: 1RS, cis, Z

One class of these pyrethroid compounds showing a remarkably high activity has the general formula I where the carbon atoms marked 1 and 3 are asymmetrical carbon atoms, and R' is selected from a group of radicals known to impart an insecticidal activity to the molecule, e.g. RS-α-cyano-3-phenoxybenzyl or S-α-cyano-3-phenoxybenzyl or 2-methylbiphenyl-3-ylmethyl or 2,3,5,6-tetrafluoro-4-methylbenzyl.

The superscripts [1], [2] etc. in the following description refer to the list of references at the end of the present description.

It is known[1] that the stereoisomeric configuration of the acid moiety of the ester Ia should have the geometry 1R, cis, Z in order to obtain maximum insecticidal activity, i.e. the absolute configuration at carbon atom 1 is R, the two hydrogen atoms at carbon atoms 1 and 3 are in cis-position, and the chlorine atom and cyclopropane group are at the same side of the carbon-carbon double bond.

Therefore, it is of great importance to be able to prepare the active isomer of I in a technically as well as economically attractive manner in order to minimize in this way the applied amount of active substance (insecticide) in the treatment of agricultural crops, habitations and the like.

From this it follows that if such compounds of formula Ia are to be prepared, it is necessary either to provide a stereospecific chemical synthetic route or to isolate the desired stereoisomer from a racemic mixture by physical separation techniques. The latter method is normally expensive and rarely used on an industrial scale.

It is known[2] that Biocartol of formula II below can be reacted with a halogenated one-carbon compound such as $CHBr_3$, $CHCl_3$ eller $CHClF_2$ in the presence of a strong base to obtain cyclopropane carboxylic acid derivatives.

It is also known[3] that the racemic compound of formula IVb below can be prepared by cyclizing 4-diazoacetoxy-5,5-dichloro-6,6,6-trifluoro-2-methyl-2-hexene in a suspension of copper(II)acetyl acetonate in boiling dioxane where the cyclopropane ring is thus formed as the last step in a reaction sequence.

Moreover, it is suggested[3] that the racemic compound of formula IVb below can be formed by reaction between esters of cis-3-formyl-2,2-dimethyl-cyclopropane carboxylic acid and 1,1,1-trichloro-2,2,2-trifluoro-ethane in the presence of zinc.

A route has now been found to the commercially important compounds of the type I where as starting material use is made of the substance Biocartol (formula II) which is easily prepared in an optically pure form IIa from the naturally occurring substance (+)-3-carene[4,5,6] or in a racemic form IIb via ozonolysis of chrysanthemic acid or derivatives thereof[3]. Trans-3-(dimethoxymethyl)-2,2-dimethyl-cyclopropane carboxylic acid methyl ester which is commercially available from, e.g., Aldrich-Chemie, is also via hydrolysis and epimerization-lactonization a source of IIb.

This synthetic route is quite specific in respect of the stereoisomery of the products such that the geometry of IIa can be found again in the product Ia. In this way costly racemate resolutions as well as yield losses to useless isomers are avoided.

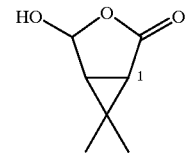

IIa: 1R, cis
IIb: 1RS, cis

Biocarcol

Here is described a number of new syntheses (see Reaction Scheme) of the (1R, cis, Z)-acid moiety in the pyrethroid esters of formula Ia (R'=H) from Biocartol IIa, going via novel intermediates IIIa and/or IVa of the invention. These synthetic methods can be used in the same way to prepare the racemic (1RS, cis, Z)-acid moiety in the pyrethroid esters of formula Ib (R'=H) from racemic Biocartol IIb, via the novel intermediate IIIb.

Here is also described synthetic routes to I (R'=H) (one-pot syntheses) from II where the intermediates III and IV are not isolated, but are recognized and characterized by means of GC, however. These synthetic methods are used for the synthesis of Ia from IIa and Ib from IIb.

Reaction Scheme

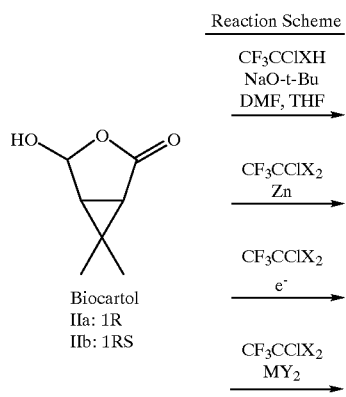

Biocartol
IIa: 1R
IIb: 1RS

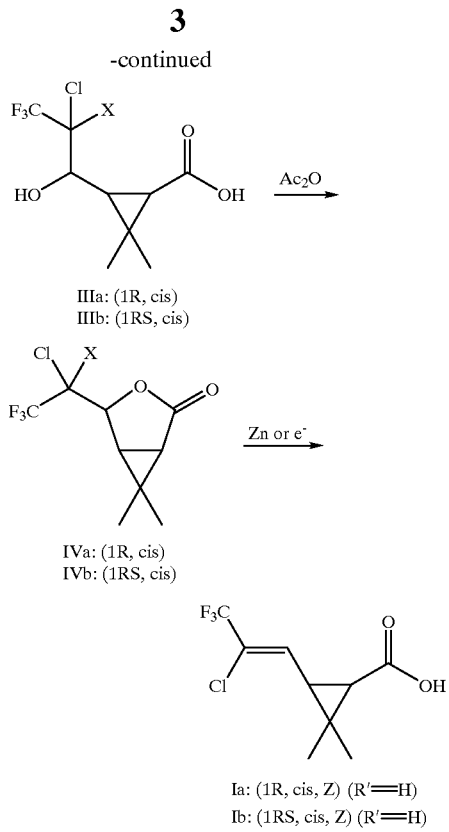

IIIa: (1R, cis)
IIIb: (1RS, cis)

IVa: (1R, cis)
IVb: (1RS, cis)

Ia: (1R, cis, Z) (R'=H)
Ib: (1RS, cis, Z) (R'=H)

The present invention relates to compounds of the general formula III or compounds of the general formula IV, wherein X represents a halogen atom, particularly chlorine.

The preferred compounds of the general formula III are cis-3-(2,2-dichloro-3,3,3-trifluoro-1-hydroxypropyl)-2,2-dimethylcylopropane carboxylic acid (IIIb, X=Cl) and 3-(2,2-dichloro-3,3,3-trifluoro-1-hydroxypropyl)-2,2-dimethyl-(1R,cis)-cyclopropane carboxylic acid (IIIa, X=Cl).

The compound IIb (X=Cl) and the compound IIIa (X=Cl) are characteristic by being ideal and novel starting materials for the synthesis of IVb (X=Cl) and IVa (X=Cl), respectively, and ultimately of Ib (R'=H) and Ia (R'=H), respectively. This is also illustrated by the above-mentioned one-pot syntheses of I from II by successive addition of reactants where III and IV occur as intermediates.

The preferred compound of the general formula IV is (1R,5S)-4-(1,1-dichloro-2,2,2-trifluoroethyl)-6,6-dimethyl-3-oxabicyclo[3.1.0]hexan-2-one of the following formula IVa (X=Cl).

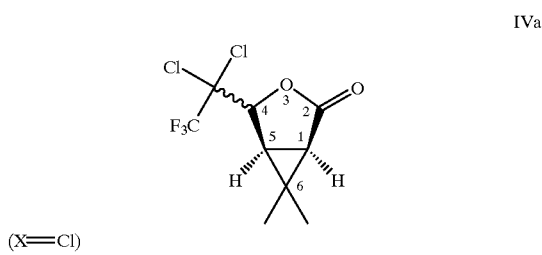

IVa (X=Cl)

The compound IVa (X=Cl) is characteristic by being an ideal and novel starting material for the synthesis of Ia (R'=H), as well as by the fact that it has surprisingly been found that the further reaction almost exclusively results in the Z-isomer of I. On account of the asymmetric carbon atom adjacent to the CXCl group and the asymmetry in the very CXCl group (for X≠Cl), the compounds IIIa and IVa (and similarly IIb and IVb) can exist in a number of isomeric forms and not necessarily in equal amounts. The proportions are seen in GC and NMR analyses. All these isomers result in the same end product Ia (resp. Ib).

NMR and GC analyses of the end products Ia and Ib show that there is preferably isolated Z-isomer, usually more than 90% of Z-isomer, and the crude products are easily purified to be more than 99% of Z-isomer.

The present invention relates to the preparation of compounds of the general formula I, wherein R' represents H, and the two hydrogen atoms on the cyclopropane ring are positioned cis to each other, by reacting compounds of the general formula II and the compound $CF_3$-$CClX_2$ wherein X represents a halogen atom, particularly chlorine or bromine, in an inert medium as for example DMF in the presence of an excess of metallic zinc, and suitably at temperatures between 0 and 150° C., preferably between 20 and 100° C. After a period of time where GC analysis of the reaction mixture shows that the starting compound II has been consumed, that the intermediates III and IV have been formed and that the end product I has been formed in a minor amount, a dehydrating agent, preferably acetic anhydride, is added, which immediately converts intermediate III into intermediate IV, as ascertained by means of GC. After a further period of time intermediate IV is converted completely into end product I, predominantly as the Z-isomer, both in optically pure and racemic form, provided that unreacted metallic zinc is permanently present.

When metallic reagents are used in the above-mentioned case, such reagents may conceivably be replaced by catalytic amounts of the same metal which is electrochemically regenerated during the reaction.

The invention is further illustrated in the following examples. Yields and purities were determined by gas and/or liquid chromatography, as well as NMR spectroscopy.

EXAMPLE 1

(Comparative Example)

Preparation of 3-(2,2-dichloro-3,3,3-trifluoro-1-hydroxypropyl)-2,2-dimethyl-(1R,cis)-cyclopropane carboxylic acid (IIIa, X=Cl) from Biocartol IIa.

To a stirred solution of 0.02 mol of IIa (2.34 g) and 0.022 mol of 1,1-dichloro-2,2,2-trifluoroethane (3.36 g) in a mixture of 5 g of dry DMF and 25 mL of THF, cooled by external cooling to −70° C., 27 mL of a 1 M solution of potassium t-butoxide are slowly added such as to keep the temperature in the reaction mixture below −55° C. Subsequent reaction at the same temperature for 30 min. takes place, and then the reaction mixture is quenched with the calculated amount of conc. HCl(aq.). After spontaneous heating to room temperature the resulting solution is poured into a water-methyl t-butyl ether mixture. The aqueous phase and the organic phase are separated and the aqueous phase is extracted with a further 2×25 mL of methyl t-butyl ether (MTBE). The combined organic phase is dried over $Na_2SO_4$ and evaporated at reduced pressure. 1.1 g of crude product is obtained having a purity of 60% measured gas chromatography. The crude product is purified by crystallization from hexan and 0.4 g of IIIa (28% of theory) is isolated, with a melting point of 126–9° C. (decomp.) and a purity according to NMR of >95%. Specific rotation: $[\alpha]_D^{25}$=−11° (1.28 g/100 mL, THF).
$^1$NMR (250 MHz, $CDCl_3$+$CD_3OD$): 1.2 ppm (s, 3H); 1.31 ppm (s, 3H); 1.7 ppm (m, 2H); 4.51 ppm (d, J=8.8 Hz, 1H); 4.8 ppm (broad signal, 2H) from the major isomer. 1.27 ppm (s, 3H); 1.39 ppm (s, 3H) from the minor isomer.

¹³C-NMR (63 MHz, CDCl₃+CD₃OD): 16.1 ppm (q); 28.4 ppm (s); 28.6 ppm (q); 29.5 ppm (d); 35.8 ppm (d); 71.4 ppm (d); 88.9 ppm (qs, 32 Hz); 122.9 ppm (qs, 282 Hz); 174.8 ppm (s).

In an identical manner cis-3-(2,2-dichloro-3,3,3-trifluoro-1-hydroxypropyl)-2,2-dimethyl-cyclopropane carboxylic acid (IIIb, X=Cl) is prepared from IIb.
Melting point 127–30° C.
¹H-NMR (250 MHzm CDCl₃): 1.24 ppm (s, 3H); 1.31 ppm (s, 3H); 1.8 ppm (m, 2H); 4.50 ppm (d, 8.6 Hz, 1H)
¹³C-NMR (63 MHz, CDCl₃); 15.4 ppm (q); 28.1 ppm (q); 29.0 ppm (d); 29.2 ppm (s); 35.7 ppm (d); 71.0 ppm (d); 887.5 ppm (qs, 39 Hz); 121.9 ppm (qs, 277 Hz); 177.4 ppm (s).

EXAMPLE 2

(Comparative Example)

Preparation of 3-(2,2,dichloro-3,3,3-trifluoro-1-hydroxypropyl)-2,2-dimethyl-(1R,cis)-cyclopropane carboxylic acid (IIIa, X=Cl) from Biocartol IIa.

13 mL of 1 M solution of potassium tert-butoxide (13 mmol) in THF are cooled to about −70° C. under an atmosphere of dry nitrogen. To this is added dropwise a mixture of 5 mmol of IIa (0.7 g), 8 mmol of 1,1-dichloro-2,2,2-trifluoroethane (1.22 g), 1.0 g of dry DMF og 5 mL of dry THF while cooling and stirring such that the temperature does not exceed −55° C. After 90 minutes a further 2 mL of potassium tert-butoxide (2 mmol) are added and immediately thereafter 2 mmol of 1,1-dichloro-2,2,2-trifluoroethane (0.31 g). This is further repeated twice at the same time interval. Thus, a total of 19 mL of potassium tert-butoxide and 14 mmol of 1,1-dichloro-2,2,2-trifluoroethane have been added. After a reaction time of 6 hours 4 mL of conc. HCl are added under continued cooling to <−55° C., whereafter the reaction mixture is allowed to stand for spontaneous heating to room temperature. The reaction mixture is worked up as in Example 1. The yield is 0.9 g of a powder IIIa (61% of theory) which is analysed by NMR to be of >95% purity.

In an identical manner cis-3(2,2-dichloro-3,3,3-trifluoro-1hydroxypropyl)-2,2-dimethyl-cyclopropane carboxylic acid (IIIb, X=Cl) is prepared from IIb.

EXAMPLE 3

Preparation of (1R, 5S)-4-(1,1-dichloro-2,2,2-trifluoroethyl)-6,6-dimethyl-3-oxabicyclo[3.1.0]hexan-2-one (IVa, X=Cl) from IIIa.

IIIa (0.005 mol; 1.52 g) dissolved in 10 mL of acetic anhydride is stirred at 85° C. for 2¼ hours, cooled to room temperature, treated with aqueous NaHCO₃ and extracted twice with MTBE which is dried over Na₂SO₄ and evaporated. 1.35 g is isolated which is purified by chromatography over silica (CH₂Cl₂). 1.23 g of IVa (purity 93.4%, GC; 83% yield) is isolated. Recrystallisation of 0.51 g of this product from 10 mL of n-hexane gives 0.31 g of colourless needles of a purity higher than 95% (NMR analysis) and a melting point of 91–93° C. Specific rotation: [α]_D^25=+5° (1.27 g/100 mL, CHCl₃)
¹H-NMR (250 MHz, CDCl₃): 1.25 ppm (s, 3H); 1.26 ppm (s, 3H); 2.13 ppm (d, J=5.9 Hz, 1H); 2.38 ppm (d, J=5.9 Hz, 1H); 4.63 ppm (s, 1H).
¹³C-NMR (63 MHz, CDCl₃): 15.1 ppm (q); 23.4 ppm (s); 25.3 ppm (q); 30.0 ppm (d); 31.6 ppm (d); 77.6 ppm (d); 85.1 ppm (qs, 34 Hz); 121.5 ppm (qs, 284 Hz); 171.9 ppm (s).

X-Ray crystallographic examinations of the recrystallized product IVa show the following crystal structure:

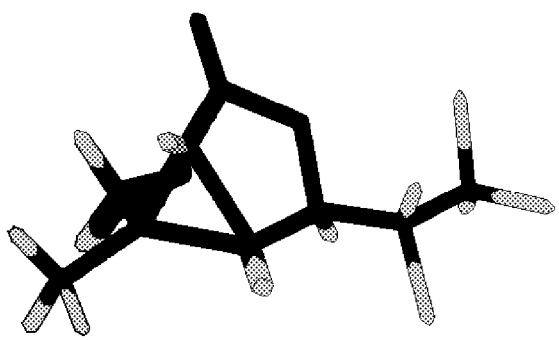

Crystal form: monoclinic: Space group: P2/1
a=9.3871(17) Å; b=10.6301(51) Å; c=6.2997(12) Å
α=90°; β=110.505(12)°; γ=90°
volume of unit cell=588.79(33) Å³
Number of molecules per unit cell, Z=2
Calculated density=1.5627 Mg/m³
F(000)=280.0000
Mo Kα radiation=0.71073 Å; μ=5.717 cm⁻¹; 298 K
The coordinates of the individual atoms in the unit cell are as shown in the following table

| ATOM | X | Y | Z |
|---|---|---|---|
| C11 | 0.3223( 2) | 0.7909 | 0.2218( 3) |
| C12 | 0.3155( 2) | 0.7445( 4) | 0.6668( 3) |
| F1 | 0.5513( 4) | 0.6180( 7) | 0.5499(10) |
| F2 | 0.4148( 6) | 0.5328( 7) | 0.2415(12) |
| F3 | 0.3865( 7) | 0.4839( 9) | 0.5457(18) |
| O1 | −0.0170( 6) | 0.5798( 7) | −0.2696( 7) |
| O2 | 0.1060( 5) | 0.5573( 5) | 0.0998( 6) |
| C1 | −0.0700( 6) | 0.7212( 8) | −0.0046( 9) |
| C2 | 0.0025( 7) | 0.6177( 8) | −0.0841( 9) |
| C3 | 0.1273( 6) | 0.6236( 7) | 0.3045( 9) |
| C4 | 0.0086( 6) | 0.7265( 8) | 0.2502( 9) |
| C5 | −0.1548( 6) | 0.6869( 7) | 0.1514( 9) |
| O6 | −0.2043( 7) | 0.5552(10) | 0.1695(10) |
| O7 | −0.2674( 8) | 0.7845(12) | 0.1647(15) |
| C8 | 0.2905( 6) | 0.6752( 7) | 0.3986( 8) |
| C9 | 0.4102( 8) | 0.5711(13) | 0.4301(19) |
| H1 | −0.1052(76) | 0.8094(88) | −0.108(11) |
| H3 | 0.1286(54) | 0.5547(63) | 0.4182(78) |
| H4 | 0.0299(61) | 0.8053(72) | 0.3330(83) |
| H6a | −0.2554 | 0.5325 | 0.2692 |
| H6b | −0.1131 | 0.5042 | 0.2146 |
| H6c | −0.2669 | 0.5305 | 0.0223 |
| H7a | −0.3201 | 0.7626 | 0.2682 |
| H7b | −0.3404 | 0.7966 | 0.0219 |
| H7c | −0.2142 | 0.8607 | 0.2216 |

In an identical manner 4-(1,1-dichloro-2,2,2-trifluoroethyl)-6,6-dimethyl-3-oxabicyclo[3.1.0]hexan-2-one (IVb, X=Cl) is prepared from IIIb.
¹H-NMR 250 MHz, CDCl₃): 1.25 ppm (s, 3H); 1.26 ppm (s, 3H); 2.13 ppm (dd, J=0.8 and 5.9 Hz, 1H); 2.38 ppm (d, J=5.9 Hz, 1H); 4.63 ppm (d, J=0.8 Hz, 1H).
¹³C-NMR. (63 MHz, CDCl₃): 15.1 ppm (q); 23.4 ppm (s); 25.3 ppm (q); 30.1 ppm (d); 31.7 ppm (d); 85.1 ppm (qs, 34 Hz); 121.5 ppm (qs, 284 Hz); 171.9 ppm (s).

EXAMPLE 4

(Comparative Example)

Preparation of cis 3-(2-bromo-2-chloro-3,3,3-trifluoro-1-hydroxypropyl-2,2-dimethyl-cyclopropane carboxylic acid (IIIb, x=Br) from Biocartol IIb.

As Example 2, but with 1-bromo-1-chloro-2,2,2-trifluoroethane instead of 1,1-dichloro-2,2,2-trifluoroethane Recrystallization from toluene gave a white powder (IIIb) having a melting point 170–2° C. and a purity higher than 95% (NMR, sum of several isomers).

$^1$H-NMR (250 MHz, DMSO-d$_6$): 1.14 ppm (s, 3H); 1.24 ppm (s, 3H); 1.53 ppm (dd, 9.1 Hz and 9.6 Hz, 1H); 1.65 ppm (d, 9.1 Hz, 1H); 4.17 ppm (d, 9.6 Hz, 1H); 6.2 ppm (broad s, 1H); 11.9 ppm (broad s, 1H).

$^{13}$C-NMR (63 MHz, DMSO-d$_6$): 15.7 (q); 27.8 ppm (q); 28.3 ppm (d); 35.8 ppm (d); 69.8 ppm (d); 79.5 ppm (qs, 30 Hz); 122.3 (qs, 282 Hz); 172.0 ppm (s).

The spectral data are from the major isomer.

EXAMPLE 5
Preparation of Z-cis-3-(2-chloro-3,3,3-trifluoro-1-propenyl)-2,2-dimethyl-cyclopropane carboxylic acid (Ib) from IIb.

A suspension or Zn powder (0.03 mol; 1.96 g) in a trifluoroethane (0.015 mol; 2.81 g) in 10 mL of dry DMF is stirred under reflux for about 4 hours at 65° C., until GC analysis shows that all of IIb has been converted into a mixture of IIIb and IVb as well as minor amounts of Ib. Acetic anhydride (0.01 mol; 1.02 g) is added and stirring continued at 60° C. for about 5 hours, it being permanently secured that unreacted Zn powder is present in the reaction mixture. The product is isolated by extraction with MTBE of the reaction mixture, to which aqueous HCl has been added. The MTBE-phase is dried over Na$_2$SO$_4$ and evaporated. Yield of Ib: 0.57 g (>95% purity, 47% of theory). Recrystallization from n-heptane gives a product of melting point 106–8° C. (The literature$^7$ reports 108–10° C. for Ib).

EXAMPLE 6
Preparation of Z-3-(2-chloro-3,3,3-trifluoro-1-propenyl)-2,2-dimethyl-(1R, 3R)-cyclopropane carboxylic acid (Ia) from IVa.

A suspension of Zn powder (0.004 mol; 0.26 g) in a solution of IVa (0.0026 mol; 0.72 g) in 3 mL of DMF is stirred at 60° C. for 7½ hours, and after cooling to room temperature 10 mL of water and 5 mL of conc. HCl are added. The mixture is extracted three times with MTBE which is dried over Na $_2$SO$_4$ and evaporated. It results in 0.65 g of crystals which according to GC analysis are almost 100% pure. Yield about 100%. Recrystallization from 10 mL of n-heptane gives 0.21 g of white crystals of melting point 105–8° C. Specific rotation: [α]$_D^{25}$=+47° (1.14 g/100 mL, CHCl$_3$)

$^1$H-NMR (250 MHz, CDCl$_3$): 1.32 ppm (s, 2×3H); 1.99 ppm (d, J=8.3 Hz, 1H); 2.23 ppm (dd, J=9.3 and 8.3 Hz, 1H); 6.87 ppm (d, J=9.3 Hz, 1H); 10.8 ppm (broad signal, 1H). At 6.58 ppm (d, J=9.6 Hz) a signal is suspected corresponding to a content of about 5% of the E-isomer which disappears completely on recrystallization of the substance.

$^{13}$C-NMR (63 MHz, CDCl$_3$): 14.9 ppm (q); 28.6 ppm (q); 29.5 ppm (s); 31.6 ppm (d); 32.7 ppm (d); 120.5 ppm (qs, 38 Hz); 122.1 ppm (qs, 271 Hz); 129.7 ppm (qd, 5 Hz); 176.6 ppm (s).

Reaction of a minor amount of Ia with an excess of thionyl chloride and subsequently with an excess of methanol gives the methyl ester of Ia. Analysis of this ester on a chiral GC column shows that it has an optical purity of >95% enantiomeric excess.

EXAMPLE 7
Preparation of Z-3-(2-chloro-3,3,3-trifluoro-1-propenyl)-2,2-dimethyl-(1R, 3R)-cyclopropane carboxylic acid (Ia) from IVa.

Use is made of an Electro Micro Flow Cell (from the firm Electrocell AB, Sweden) with a lead cathode and a graphite anode, the electrodes having each an area of 10 cm$^2$. As an ion selective membrane use is made of Selemion® CMV, a cation selective membrane from the Japanese firm Asahi Glass Co. 10 mL of conc. sulphuric acid are carefully dissolved in 300 mL of methanol. 150 mL are poured in as a catholyte and 150 mL as an anolyte. The circulating pumps are started up, and when the temperature has stabilized at 50° C., a solution of IVa (0.0072 mol; 2.00 g) in 10 mL of methanol is added to the catholyte.

The electrode cables are affixed, the current supply is started and the constant voltage is adjusted to 4.0 volts. At the time=0 the current is 0.30 amp. Samples are taken about every 30 minutes, and after 270 min. the current is switched off and the cables removed. The current at the end of the experiment was 0.20 amp.

The catholyte is discharged and worked up by distilling off methanol on a rotary evaporator at 50° C. and 100 mm Hg after addition of 50 mL of water. The aqueous phase is then extracted with methyl t-butyl ether which is dried and evaporated. 1.68 g of an oil is obtained which is mixed with 10 mL of 2 N NaOH(aq.) and allowed to stand with stirring for 2 hours. The aqueous phase is acidified with conc. HCl(aq.) and extracted with methyl t-butyl ether which is dried and evaporated. 1.33 g of crystals is obtained which according to GC analysis are of >95% purity. Yield about 750%.

EXAMPLE 8
Preparation of Z-3-(2-chloro-3,3,3-trifluoro-1-propenyl)-2,2-dimethyl-(1R,3R)-cyclopropane carboxylic acid (Ia) from IIa.

A suspension of Zn powder (0.045 mol; 2.94 g) in a solution of IIa (0.015 mol; 2.13 g) and 1,1,1-trichloro-trifluoroethane (0.038 mol; 7.12 g) in 25 mL of dry DMF is stirred in a 50 mL Teflon-lined autoclave for about 2 hours at 50° C. The autoclave is opened and GC analysis shows that all of IIa has been converted into a mixture of IIIa and IVa as well as minor amounts of Ia. Acetic anhydride (0.018 mol; 1.84 g) is added, the autoclave is closed, heated for 15 minutes at 50° C. and reopened. GC analysis shows that all of IIIa has been converted into IVa. Zn powder (0.018 mol; 1.18 g) is added, the autoclave is closed again and allowed to stand with stirring at 70° C. for about 2 hours. The autoclave is opened and the product isolated by extraction with MTBE of the reaction mixture to which aqueous HCl has been added. The MTBE phase is dried over Na$_2$SO$_4$ and evaporated. Yield of Ia: 2.48 g (>95% purity, 68% of theory). Recrystallization from n-heptane gives a product with melting point 106–7° C.

List of references:
[1] British Patent 2 000 764 (Mar. 23, 1977), ICI
[2] Danish patent application 2849/78 (Jun. 26, 1978), Roussel-Uclaf, S. A.
[3] M. Fujita, K. Kondo and T. Hiyama, Tetrahedron Letters, 27, 2139–2142 (1986) resp. Bull. Chem. Soc. Jpn., 60, 4385–4394 (1987)
[4] Arun K. Mandal, et al., Tetrahedron, 42, 5715 (1986)
[5] D. Bakshi, V. K. Mahindroo, R. Soman, S. Dev, Tetrahedron, 45, 767–774 (1989)
[6] Danish patent application DK 5633/78 (Dec. 14, 1978), Shell Internationale Research Maatschappij B. V.
[7] U.S. Pat. No. 4,333,950 (Jun. 8, 1982), FMC Corporation.

We claim:
1. A process for the preparation of compounds of the general formula I

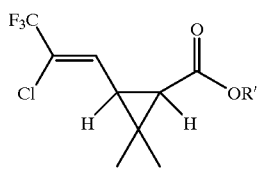

wherein R' represents H and the two hydrogen atoms on the cyclopropane ring are positioned cis to each other, comprising reaction between a compound of the general formula II

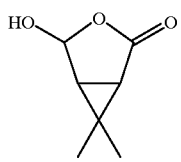

and the compound $CF_3$—$CClX_2$, wherein X represents a halogen atom, in an inert medium in the presence of Zn and suitably at temperatures between 0 and 150° C., during which reaction the compounds III and IV

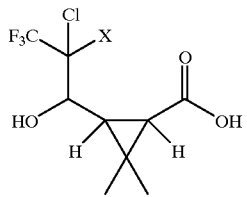

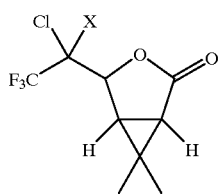

occur as intermediates which are not isolated, and when after a period of time analyses show that the starting compound II has been substantially consumed, that the above intermediates III and IV have been formed, and that the end product I has been formed in a minor amount, addition of a dehydrating agent which immediately converts intermediate III into intermediate IV and after a further period of time converts intermediate IV substantially completely into the end product I predominantly as the Z-isomer, in both optically pure and racemic form, care being taken that unreacted metallic zinc is permanently present.

2. A process according to claim 1, wherein the inert medium is DMF.

3. A process according to claim 1, wherein the dehydrating agent is acetic anhydride.

4. A process according to claim 1, wherein part or all of the metallic reagent is replaced by electrochemically generated metallic material.

5. The compound 3-(2,2-dichloro-3,3,3-trifluoro-1-hydroxypropyl)-2,2-dimethyl-(1R,cis)-cyclopropane carboxylic acid (IIIa, X=Cl).

6. The compound cis-3-(2,2-dichloro-3,3,3-trifluoro-1-hydroxypropyl)-2,2-dimethyl-cyclopropane carboxylic acid (IIIb, X=Cl).

7. The compound (1R,5S)-4-(1,1-dichloro-2,2,2-trifluoro-ethyl)-6,6-dimethyl-3-oxabicyclo[3.1.0]hexan-2-one (IVa, X=Cl).

8. The process of claim 1 wherein X is chlorine or bromine.

9. The process of claim 2 wherein X is chlorine or bromine.

10. The process of claim 3 wherein X is chlorine or bromine.

11. The process of claim 4 wherein X is chlorine or bromine.

12. The process according to claim 1 wherein the reaction between the compound of formula II and the compound $CF_3$—$CClX_2$ is at a temperature between 20 and 100° C.

13. The process according to claim 2 wherein the reaction between the compound of formula II and the compound $CF_3$—$CClX_2$ is at a temperature between 20 and 100° C.

14. The process according to claim 3 wherein the reaction between the compound of formula II and the compound $CF_3$—$CClX_2$ is at a temperature between 20 and 100° C.

15. The process according to claim 4 wherein the reaction between the compound of formula II and the compound $CF_3$—$CClX_2$ is at a temperature between 20 and 100° C.

16. The process according to claim 8 wherein the reaction between the compound of formula II and the compound $CF_3$—$CClX_2$ is at a temperature between 20 and 100° C.

17. The process according to claim 9 wherein the reaction between the compound of formula II and the compound $CF_3$—$CClX_2$ is at a temperature between 20 and 100° C.

18. The process according to claim 10 wherein the reaction between the compound of formula II and the compound $CF_3$—$CClX_2$ is at a temperature between 20 and 100° C.

19. The process according to claim 11 wherein the reaction between the compound of formula II and the compound $CF_3$—$CClX_2$ is at a temperature between 20 and 100° C.

* * * * *